United States Patent [19]

Noriyuki et al.

[11] Patent Number: 5,385,985
[45] Date of Patent: Jan. 31, 1995

[54] CYCLIC UREA DERIVATIVE

[75] Inventors: Tsuboniwa Noriyuki, Higashiosaka; Urano Satoshi, Tsuzuki; Umemoto Hirotoshi, Uji; Sakamoto Hiroyuki, Nishinomiya; Tobinaga Kenshiro, Kawanishi; Tsuchiya Yasuyuki, Hirakata, all of Japan

[73] Assignee: Nippon Paint Co., Ltd., Osaka, Japan

[21] Appl. No.: 947,092

[22] Filed: Sep. 17, 1992

Related U.S. Application Data

[63] Continuation of Ser. No. 456,651, Dec. 29, 1989, abandoned.

[30] Foreign Application Priority Data

Dec. 29, 1988 [JP] Japan ................... 63-331997

[51] Int. Cl.⁶ .................................. C08L 77/00
[52] U.S. Cl. .................. 525/420; 544/296; 544/316; 544/318; 548/318.1; 548/318.5; 548/320.1; 528/45; 528/73; 525/437; 525/453; 525/523
[58] Field of Search ............... 525/420, 437, 453; 528/62, 68; 544/316, 318, 296; 548/318, 320

[56] References Cited

U.S. PATENT DOCUMENTS 3,686,204 8/1972 Munz et al. ................ 548/320

FOREIGN PATENT DOCUMENTS 57-81477 5/1982 Japan .
1255751 12/1971 United Kingdom .
1259050 1/1972 United Kingdom .

OTHER PUBLICATIONS

James N. Chilley et al., J. Org. Chem. 29(11), 3347–50 (1964).
R. A. Bylum et al., Chemical Abstracts, 91(17): 140779q (Oct. 22, 1979).
R. A. Bylum et al., Chemical Abstracts, 92(1): 6463z (Jan. 7, 1980).
*Institute for Production and Development Science,* Chemical Abstracts, 95(5): 43113t (Aug. 3, 1981).
K. Nagarajan et al., Chemical Abstracts, 98(25): 215526K (Jun. 20, 1983).
H. Kondo et al., Bulletin Of The Chemical Society Of Japan, vol. 55, No. 10 (Oct. 1982), pp. 3347–3348.
J. N. Tilley et al., Journal Of Organic Chemistry, vol. 29, No. 11 (Nov. 1964), pp. 3347–3350.
H. Ulrich et al., Journal Of Organic Chemistry, vol. 43, No. 8 (1978), pp. 1544–1546.
R. K. Olsen et al., Journal Of Organic Chemistry, vol. 47, No. 24 (Nov. 19, 1982), pp. 4605–4610.

*Primary Examiner*—John Kight, III
*Assistant Examiner*—R. Johnson
*Attorney, Agent, or Firm*—Foley & Lardner

[57] ABSTRACT

Disclosed is cyclic urea derivatives represented by the following formula (A):

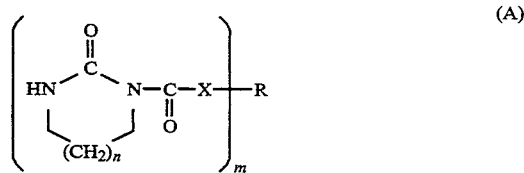

wherein n is an integer of 0 or 1; m is an integer of 1 to 15; X is oxygen, sulfur or $-NR_1-$ ($R_1$ is hydrogen or an alkyl group having 1 to 5 carbon atoms); R is an alkyl-, cycloalkyl -, aryl-, aralkyl-, alkaryl- and glycidyl group having 1 to 27 carbon atoms, or an alkyl-, cycloalkyl-, aryl-, aralkyl- and alkaryl group containing at least one

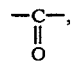

O, S and N and having 1 to 27 carbon atoms with a molecular weight of 15 to 500, said groups substituted by glycidyl-, hydroxylic-, nitro groups, halogens, cyano-, formyl- or amino groups, or polyester-, polyether-, polyurethane and polyamide groups having a molecular weight of 500 to 100,000.

11 Claims, No Drawings

CYCLIC UREA DERIVATIVE

This application is a continuation of U.S. application Ser. No. 07/456,651 filed Dec. 29, 1989, now abandoned.

FIELD OF THE INVENTION

The present invention relates to novel cyclic urea derivatives and a method of producing the same.

BACKGROUND OF THE INVENTION

It is disclosed in Japanese Patent Publication No. 240075/1988 that cyclic urea compounds represented by the following formula (P) are contained in thermosetting resin composition.

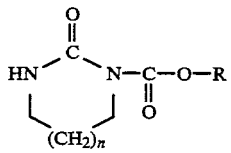

A heterocyclic ring of these cyclic urea compounds is limited by a seven-member ring or more (that is n is 2 or more). A five-member ring and a six-member ring are not disclosed.

Compounds containing a five- to seven-member ring which have no oxygen connected directly to a carbonyl group of cyclic urea derivatives represented by the above described formula (P) are disclosed in J. Org. Chem., Vol, 43, No. 8. 1978 by Henri Ulrich et al. This report is characterized by that the compounds containing a five-member ring and a six-member ring do not cause a ring-opening by a thermal decomposition which is one of specific features of a cyclic urea structure. The following compound represented by the following formula (Q) is also disclosed in J. Org. Chem. 29 (11), 3347-50(1964) by James N. Tilley et al.

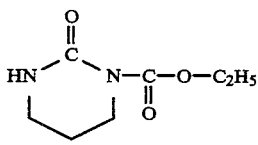

This compound is obtained by a complicated method.

SUMMARY OF THE INVENTION

The present inventors investigated a synthesis of useful cyclic urea compounds with the result that novel cyclic urea derivatives, which form a useful isocyanate group after the ring-opening by the thermal decomposition of the five-member ring and six-member ring, are synthesized.

Thus, the present invention provides cyclic urea derivatives represented by the following formula (A):

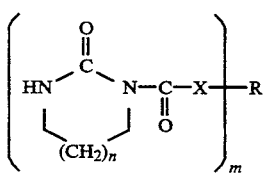

wherein n is an integer of 0 or 1; m is an integer of 1 to 15; X is oxygen, sulfur or —NR$_1$— (R$_1$ is hydrogen or an alkyl group having 1 to 5 carbon atoms); R is an alkyl-, cycloalkyl -, aryl-, aralkyl-, alkaryl- and glycidyl group having 1 to 27 carbon atoms, or an alkyl-, cycloalkyl-, aryl-, aralkyl- and alkaryl group containing at least one

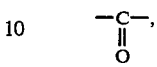

O, S and N and having 1 to 27 carbon atoms with a molecular weight of 15 to 500, said groups substituted by glycidyl-, hydroxylic-, nitro groups, halogens, cyano-, formyl- or amino groups, or polyester-, polyether-, polyurethane and polyamide groups having a molecular weight of 500 to 100,000.

DETAILED DESCRIPTION OF THE INVENTION

A first method of synthesizing the cyclic urea derivatives according to the present invention consists in a reaction of cyclic urea represented by the following formula (B):

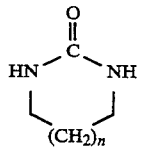

wherein n is same as in the formula (A), with compounds represented by the following formula (C):

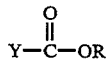

wherein Y is halogen or OR" (R" is same as R in the formula (A) and R is same as in the formula (A). A cyclic urea derivative obtained by this reaction is a compound according to said formula (A) in which X is oxygen. The compounds represented by the formula (C) are in general compounds obtained by a reaction of phosgen with ROH. The compounds (C) include methyl chloroformate, n-propyl chloroformate, isopropyl chloroformate, ethoxyethyl chloroformate, sec-butyl chloroformate, benzyl chloroformate, 2-ethylhexyl chloroformate, methoxyethyl chloroformate, tetradodecyl chloroformate, hexadecyl chloroformate, phenyl chloroformate and the like.

This reaction is conducted at temperatures of 0° to 200° C., preferably 50° to 150° C., in the presence of a suitable solvent. In the reaction, basic catalysts, such as triethyl amine, 1,4-diazabicyclo[2,2,2]octane, 1,8-diazacyclo[5,4,0]undesene-7, pyridine, sodium methoxide, sodium ethoxide, t-butoxy potassium and hexamethyl phosphoric triamide, may be used if necessary, or may not be used. The suitable solvent is a solvent having no active hydrogen. It may be selected from the group consisting of for example hydrocarbons, halogenated hydrocarbons, ethers and esters. Preferred are aliphatic hydrocarbons (such as, pentane, hexane and heptane), aromatic hydrocarbons (such as, benzene, toluene and xylene), alicyclic hydrocarbons (such as cyclohexane, methylcyclohexane and decaline), petroleum hydrocarbons (such as, petroleum ether and petroleum benzine), halogenated hydrocarbons (such as, carbon tetrachloride, chloroform and 1,2-dichloroethane), ethers (such as, ethyl ether, isopropyl ether, anisole, dioxane and tetrahydrofurane), ketones (such as, acetone, metylethyl ketone, methylisobutyl ketone, cyclohexanone, acetophenone and isophorone), esters (such as, ethyl acetate and butyl acetate, acetonitrile, dimethylformamide, dimethylsulfoxide and the like. These compounds may be used singly or in combination. In the reaction, a polymerization inhibitor may be added in case of need but it is not essential.

A cyclic urea derivative, in which X is —NH—, according to the present invention is obtained by a reaction of the above described cyclic urea with isocyanate compounds represented by the following formula (E):

$$R—(N=C=O)_m \tag{E}$$

wherein R and m are same as in the formula (A). The isocyanate compounds used here include aliphatic compounds, such as trimethylene monoisocyanate, tetramethylene diisocyanate, pentamethylene monoisocyanate, hexamethylene diisocyanate, 1,2-propylene diisocyanate, 1,2-butylene monoisocyanate, 2,3-butylene diisocyanate, 1,3-butylene monoisocyanate, ethylidine diisocyanate and butylidine monoisocyanate; cycloalkylene compounds, such as 1,3-cyclopentane diisocyanate, 1,4-cyclohexane monoisocyanate and 1,2-cyclohexane diisocyanate; aromatic compounds, such as m-phenylene diisocyanate, 1,5-naphthalene monoisocyanate, 4,4'-diphenyl diisocyanate, 1,5-naphthalene monoisocyanate and 1,4-naphthalene diisocyanate; aliphatic-aromatic compounds, such as 4,4'-diphenylenemethane diisocyanate, 2,4- or 2,6-tolylene monoisocyanate or mixtures thereof, 4,4'-toluidine diisocyanate and 1,4-xylylene diisocyanate; nucleus-replaced aromatic compounds, such as dianisidine diisocyanate, 4,4''-diphenyl ether monoisocyanate and chlorodiphenylene diisocyanate; triisocyanates, such as triphenylmethan-4,4',4''-triisocyanate, 1,3,5-triisocyanatobenzene and 2,4,6-triisocyanatotoluene; tetraisocyanates, such as 4,4'-diphenyldimethylmethane-2,2',5,5'-tetraisocyanate; polymerized polyisocyanates, such as toluilene diisocyanate dimer and trimer; and the like.

This reaction is in general conducted at temperatures of 25° to 200° C., preferably 50° to 100° C., in a suitable solvent. The suitable solvent includes the solvent mentioned above. In this reaction, catalysts, for example tin compounds (dibutyltin laurate, dibutyltin oxide, FASCAT 4102 ®(M&T CHEMICALS INC.), TK-1, 1L (TAKEDA)), mixture catalysts (dimethyltin diiodide/tetraphenyl antimony iodide, dimethyltin diiodide/hexamethyl phosphoric triamide), acidic compounds (p-toluenesulfonic acid, dodecylbenzenesulfonic acid, sulfuric acid, hydrochloric acid, nitric acid, trifluoroboron ethelate), basic compounds (triethyl amine, 1,4-diazabicyclo-[2,2,2]-octane, 1,8-diazabicyclo-[5,4,0]-undecene-7, pyridine, sodium methoxide, sodium ethoxide, t-butoxy potassium hexamethylphosphoric triamide), metal oxides or salts of metals (manganese acetate, cobalt acetate, calcium acetate, lithium acetate, zinc acetate, magnesium acetate, antimony trioxide, lead dioxide, ferric chloride, aluminium triisopropoxide, tetraisopropoxide) and the like, may be used.

The most general method of producing the cyclic urea compounds according to the present invention consists in a reaction of compounds represented by the following formula (F):

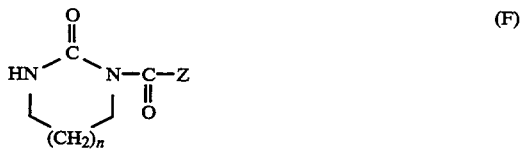

wherein Z is halogen, an alkoxy-, aryloxylic- or aralkyloxylic group having 1 to 15 carbon atoms; n is same as in the formula (A), with compounds represented by the following (G):

$$R—(X—H)_m \tag{G}$$

wherein R and X are same in the formula (A), to replace Z by R-X. The compounds represented by the formula (F) can be easily obtained by a reaction of said cyclic urea compounds (B) with phosgene itself or compounds obtained by a reaction of phosgene with ZOH. In addition, the compounds (G) used in the present invention are in general used in the form of active hydrogen-containing compounds having a carbon atom directly connected to oxygen, sulfur and nitrogen. Such the active hydrogen-containing compounds include alcohols [X=O], for example m=1 R: methanol, ethanol, stearyl alcohol, benzyl alcohol, phenanthyl alcohol, phenol, methylphenol bromophenol, glycidyl alcohol;

m=2 : ethylene glycol, diethylene glycol, triethylene glycol, 1,3-butane diol, 1,10-decane diol, pentaethylene glycol, 2,5-furan dimethanol, 1,2-cyclohexane diol, dicyclohexyl-4,4'-diol, 1,2-benzene dimethanol, 2,2-bisphenol;

m>3: glycerol, trimethylol propane, 1,2,3-pentane triol, pentaerythritol, dipentaerythritol, neopentyl glycol, lactose, xylose, mannitol, polyester polyol, polyether polyol, epoxy resins;

Amines [X=N], for example methylamine, ethylamine, propylamine, stearylamine, benzylamine, aniline, dimethylamine, methylethylamine, diethylamine, methylbenzylamine, ethylenediamine, 1,2-diaminopropane, 1,8-diaminooctane, 1,2-phenylenediamine, 2,4-diaminotoluene, N-(2-aminoethyl)-1,3-propanediamine, N,N-bis(2-aminoethyl)-1,3-propanediamine, N,N'-bis(3-aminopropyl)-1, 3-propanediamine;

aminoalcohols, for example dimethylaminoethyl alcohol, dimethylaminoethyl alcohol, dimethylaminopropyl alcohol, m-dimetylamino phenol, N-methyl-N-phenylaminoethyl alcohol, N-ethyl-N-benzylaminoethyl alcohol, pyrolidinoethyl alcohol, pyrolidinopropyl alcohol, morpholinoethyl alcohol, 2-amino-2-methyl-1-propanol, 2-amino-1-butanol, 2-amino-1-hexanol, ethanol amine;

oximes, for example acetoaldehyde oxime, acetone oxime, methylethyl ketone oxime, phenylmethyl ketone oxime, acetylacetone oxime;

thiols, for example ethyl thiol, propyl thiol, cyclohexyl thiol, phenyl thiol, naphthyl thiol, 1,2-ethane dithiol, 2,3-butane dithiol, 1,2-benzene dithiol;

polyester polyol compounds, for example polyether polyols obtained by adding polyalkylene glycols (for example polyethylene glycol, polypropylene glycol, polytetramethylene glycol, polyhexamethylene glycol) or alkylene oxides (for example ethylene oxide, propylene oxide, tetrahydrofuran) to polyols (for example ethylene glycol, diethylene glycol, propylene glycol, dipropylene glycol, glycerol, trimethylol propane, 1,3- butane diol, 1,4-butane diol, 1,5-hexane diol, 1,2,6-hexane triol, pentaerythritol, sorbitol, sorbitan, sucrose) and the like;

epoxy compounds, for example bisphenol A type epoxy resins, bisphenol F type epoxy resins, polyvalent carboxylic ester type epoxy resins, epoxidized type resins of aliphatic unsaturated compounds and the like;

star polymer compounds, for example star polymers having an active hydrogen at an end thereof obtained by a cation polymerization of pentol and ethylene oxide and the like;

polyester polyol compounds, for example polyester polyols obtained by a condensation reaction of polybasic acids (for example phthalic acid, isophthalic acid, terephthalic acid, tetrahydrophthalic acid, tetrachlorphthalic acid, tetrabromphtalic acid, hexahydrophthalic acid, hymic acid, headic acid, succinic acid, maleic acid, fumalic acid, adipic acid, sebacic acid, dodecenylsuccinic acid, pyromellitic acid) or anhydrides thereof and polyvalent alcohols (for example ethylene glycol diethylene glycol, propylene glycol, dipropylene glycol, glycerol, trimethylol propane, 1,3-butane diol, 1,6-hexane diol, neopentyl glycol, 1,2,6-hexane triol, polyester polyols obtained by a reaction of the above described polyvalent alcohols, epoxy compounds (for example Cardula E, n-butyl glycidyl ether, allyl glycidyl ether) and said polybasic acids, polyester polyols obtained by a reaction of the above described epoxy compounds and the above described polybasic acids, alkyd type polyols obtained by a reaction of higher fatty acids (soybean oil, linseed oil, saffron oil, coconut oil, dehydrated castor oil, paulownia oil, rosin), the above described polybasic acids and the above described polyvalent alcohols, polymerized type polyester polyols obtained by a ring-opening polymerization of ε-caprolactam, ε-caprolactone, γ-valelolactone, δ-valelolactone and β-methylvalelolactone, and the above described polyvalent alcohols and the like;

polyurethane polyol compounds, for example polyurethane polyols obtained by an addition reaction of for example isocyanate compounds (for example ethylene diisocyanate, propylene diisocyanate, tetramethylene diisocyanate, hexamethylene diisocyanate, 1-methyl-2,4-diisocyanate cyclohexane, 1-methyl-2,6-diisocyanate cyclohexane, ω,ω'-diisocyanate diethylbenzen, ω,ω'-diisocyanate dimethylaminotoluene, ω,ω'-diisocyanate dimethyl xylene, ω,ω'-diisocyanate diethyl xylene, lysin diisocyanate, 4,4'-methylenebis(cyclohexylisocyanate), 4,4'-ethylenebis(cyclohexylisocyanate), ω,ω'-diisocyanate-1,3-dimethyl benzene, ω,ω'-diisocyanate-1,4-dimethyl benzene, isophorone diisocyanate, 2,4-toluilene diisocyanate, 2,6-toluilene diisocyanate, 1,5-naphthylene diisocyanate, 4,4-methylenebis(phenylisocyanate), triphenylmethane triisocyanate or polymers thereof to an excessive amount of low molecular polyols (for example ethylene glycol, propylene glycol, 1,3-butyl glycol, neopentyl glycol, 2,2,4-trimethyl-1,3-pentane diol, hexamethylene glycol, cyclohexane dimethanol, trimethylol propane, hexane triol, glycerine, sorbitol sorbitan, sucrose, pentaerythritol and the like), polyurethane polyols obtained by an addition reaction of polyol compounds having relatively low molecular weights of said polyether polyols, polyester polyols, polymerized type polyester polyols and acrylic polyols to isocyanate compounds such as monoisocyanate, diisocyanate and triisocyanate and the like;

polyamide amine compounds, for example polyamide amine compounds obtained by an addition reaction of the above described isocyanate compounds to compounds such as ethylene diamine, 1,2-diaminopropane, 1,4-diaminobutane, 1,2-phenylene diamine and N-(2-aminoethyl)-1,3-propane diamine and the like.

This reaction is in general conducted at temperatures of 0° to 200° C., preferably 50° to 70° C., by the use of the above described solvents having no active hydrogen. In the synthesis, catalysts may be used in case of need. In the case where X is oxygen, tin-containing catalysts are suitable while in the case where X is —NR$_1$, the reaction makes progress without using catalysts.

According to the present invention, various kinds of cyclic urea derivative can be formed by variously changing R.

The cyclic urea derivatives according to the present invention form compounds having one or two isocyanate groups upon heating, as shown in the following reaction equation:

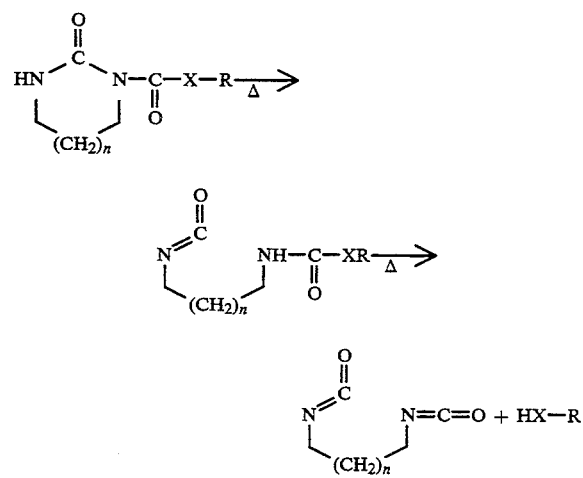

Accordingly, since the compounds having isocyanate groups are in general used as the curing agents, the cyclic urea derivatives according to the present invention are useful as compounds latently containing isocyanate curing agents. In addition, the derivatives according to the present invention can be used also as intermediated products for a synthesis of various kinds of other compound.

EXAMPLE

The present invention is below in more detail described with reference to the preferred embodiments but is not limited by these preferred embodiments.

Example 1

Phenoxycarbonylpropyleneurea

Propyleneurea (730 g, 7.3 mol), triethylamine (404 g, 4 mol) and dichloroethane of 1.5 liters were charged in a reaction vessel and heated to 82° to 85° C. Then, a solution of benzyl chloroformate (604 g, 4.0 mol) in dichloroethane of 0.5 liters was added drop by drop to the heated mixture in about one hour followed by continuing to heat with stirring for further one hour. The resulting solution was condensated. Crude crystals were washed with water and then dried. Phenoxycarbonylpropyleneurea of 438 g (49.3%) was obtained by refining by the column chromatography.

NMR (1H): 7.40 to 7.17 (m), 3.89 (t), 3.35(dt), 2.27 (tt) IR (cm$^{-1}$):3240, 1780, 1675 Melting point: 149° to 151° C.

Example 2

Ethoxycarbonylpropyleneurea

Propyleneurea of 30.0 g (0.3 mol), ethylchloroformate of 10.9 g (0.1 mol) and dichloroethane of 100 g were charged in a reaction vessel and refluxed at 85° to 88° C. A solution of triethylamine of 10.1 g (0.1 mol) in dichloroethane of 250 g was added drop by drop to the refluxed mixture in 2.5 hours followed by continuing for further 2 hours. The resulting solution was condensated and a crude product was refined by the column chromatography to obtain ethoxycarbonylpropyleneurea of 2.2 g (12.7%).

NMR (1H): 6.26, 4.28 (q), 3.77 (t), 3.35 (dt), 1.97 (tt), 1.34 (t) IR (cm$^{-1}$): 3250, 1710, 1660 Melting point: 99° to 100° C.

Example 3

N-(2-hydroxyethyl)aminocarbonylpropyleneurea

Phenoxycarbonylpropyleneurea of 1.0 g (4.5 mmol) and ethanolamine of 0.5 g (8.2 mmol) were dissolved in dioxane by heating at 50° C. The resulting solution was stirred for 30 minutes. The resulting white precipitation was filtrated and rinsed with ether to obtain the aimed substance of 790 mg (96%).

NMR (1H): 7.27, 4.70 (t), 3.84 (t), 3.43 (t) 3.30 (t), 3.20 (t), 3.12 (dt), 1.78 IR (cm$^{-1}$]): 3350, 1710, 1630 Melting point: 151° to 153° C.

Example 4

Ethylene glycol-di-(ethyloxycarbonylpropyleneurea)ether

Phenoxycarbonylpropyleneurea of 10 g (45.5 mmol) and triethylene glycol of 3.4 g (22.7 mmol) were dissolved in dioxane of 50 ml by heating. The resulting mixture was stirred for 10 hours as it is and the resulting solution was concentrated. A crude product was refined by the column chromatography to obtain the aimed substance of 1.8 g (15%).

NMR (1H): 5.99, 4.36 (t), 3.7 to 3.6 (m), 3.30 (dt), 1.96 (tt) IR (cm$^{-1}$): 3300, 1760, 1700 $C_p$: 62976 (EH type 25° C.) Melting point 225° to 230° C.

Example 5

N-benzylaminocarbonylpropyleneurea

Phenoxycarbonylpropyleneurea of 1 g (4.5 mmol) and benzylamine of 1 g (9.3 mmol) were dissolved in dioxane of 40 ml by heating to 50° C. The resulting solution was heated with stirring for 30 minutes as it is. After confirming the completion of the reaction by the thin layer chromatograpy, the reaction product was condesated. The obtained crude crystals were washed with ether to obtain the aimed substance of 975 mg (93%).

NMR (1H): 9.54, 7.29 (m), 4.49 (d), 3.87 (t), 3.37 (dt), 1.94 (tt). IR (cm$^{-1}$): 3225, 1715, 1680 Melting point: 159° to 162° C. (colorless needle-like crystal)

Example 6

Hexamethylene diaminocarbonylpropyleneurea

Phenoxycarbonylpropyleneurea of 0.89 g (4 mmol) and hexamethylenediamine of 0.24 g (2 mmol) were dissolved in dioxane of 20 ml by heating. After one hour, the completion of the reaction was confirmed by the thin layer chromatography and then the reaction product was condensated. The obtained crude product was washed with ether to obtain the aimed substance of 705 mg (94%).

NMR (1H): 9.23, 3.26 (m), 5.42, 1.92 (tt) 3.83 (t), 1.54 (m), 3.33 (dt), 1.35 (m) IR (cm$^{-1}$): 3300, 1700, 1630 Melting point: 196° to 198° C. (colorless prismatic crystal)

Example 7

Ethoxycarbonylpropyleneurea

Phenoxycarbonylpropyleneurea of 1 g (4.5 mmol) and ethanol of 10 g (21.7 mmol) were dissolved in dioxane of 20 ml by heating. Dibutyltin dilaurate of 10 mg (1%) was added to the resulting solution and the resulting mixture was heated for 5 hours with stirring. After confirming the completion of the reaction by the thin layer chromatography, the reaction product was concentrated and the resulting crude crystals were washed with ether to obtain the aimed substance of 567 mg (80%).

NMR(1H): 6.26, 4.28 (g), 3.77 (t), 3.31 (dt) 1.97 (tt), 1.34 (t) IR (cm$^{-1}$): 3250, 1700, 1682, 1660 Melting point : 99° to 100° C.

Example 8

Benzyloxycarbonylpropyleneurea

A mixture of phenoxycarbonylpropyleneurea of 1.0 g (4.5 mmol), benzyl alcohol of 2.4 g (22.2 mmol), dibutyltin dilaurate of 20 mg (0.6 wt %) and dimethylaminopyridine of 20 mg (0.6 wt %) was heated for 3 hours at 100° C. with stirring. After confirming the completion of the reaction by the thin layer chromatograpy, the reaction product was concentrated and the resulting crude substance was separated by the chromatography to obtain the aimed substance of 600 mg (56.4%).

NMR (1H): 7.34 (m), 5.52 (br), 5.28 (s), 3.78 (t) 3.32 (td), 1.96 (tt) IR (cm$^{-1}$): 3225, 3120, 1780, 1725, 1700 Melting point: 108° to 110° C. (colorless prismatic crystal)

Example 9

4-hydroxyphenyloxycarbonylpropyleneurea

Phenoxycarbonylpropylenenurea of 1.1 g (5 mmol), hydroquinone of 1.1 g (10 mmol) and dibutyltin dilaurate of 20 mg (2 wt %) were dissolved in dioxane of 30 ml by heating. The resulting solution was refluxed for 4 hours at 100° C. to form white precipitations. These precipitations were filtrated and washed with methanol to obtain the aimed substance of 840 mg (67%).

NMR (1H): 6.97 (d), 6 79 (d), 3.71 (t), 3.15 (brt), 1.88 (t), 9.40 IR(cm$^{-1}$): 3340, 1780, 1660 Melting point: 225° to 230° C.

Example 10

Hexamethylenedioxycarbonylpropyleneurea

Hexamethylene diol of 10.7 g (0.091 mol) and phenoxycarbonylpropyleneurea of 40 g were dissolved in dioxane of 300 g at an elevated temperature, to which dibutyltin dilaurate of 1 g was added. The resulting solution was mixed with heating at 85° C. for 8 hours. The reaction product was concentrated and the crude product was washed with ether. The washed product was purified with benzene by a column chromatography method to obtain hexamethylenedioxycarbonylpropyleneurea of 18.3 g (50% yield).

NMR: 6.71 (b,s), 4.21 (t), 3.75 (m), 3.32 (d,t), 1.88–1.47 (m) Melting point:74°–77° C.

What is claimed is:

1. A cyclic urea derivative represented by formula (A)

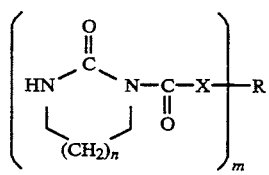

wherein,
- (a) when n is 0 or 1, m is 1, and X is oxygen, R is a $C_{3-27}$ cycloalkyl, $C_{6-27}$ aryl, $C_{7-27}$ aralkyl, $C_{7-27}$ alkaryl, $C_{3-27}$ glycidyl group or a $C_{3-27}$ alkyl, $C_{3-27}$ cycloalkyl, $C_{6-27}$ aryl, $C_{7-27}$ aralkyl, $C_{7-27}$ alkaryl group containing at least one radical selected from the group consisting of

O, S and N having a molecular weight of 15 to 500, said groups being unsubstituted or substituted with at least one substituent selected from the group consisting of glycidyl, hydroxyl, nitro, halogen, cyano, formyl, amino, polyesters of a molecular weight 500 to 100,000, polyethers of molecular weight 500 to 100,000, polyurethanes of molecular weight 500 to 100,000, and polyamides of molecular weight of 500 to 100,000;

- (b) when n is 0, m is 1, and X is sulfur, R is a $C_{3-27}$ cycloalkyl, $C_{6-27}$ aryl, $C_{7-27}$ aralkyl, $C_{7-27}$ alkaryl, $C_{3-27}$ glycidyl group, or a $C_{3-27}$ alkyl, $C_{3-27}$ cycloalkyl, $C_{6-27}$ aryl, $C_{7-27}$ aralkyl, $C_{7-27}$ alkaryl group having a molecular weight of 15 to 500 and containing at least one radical selected from the group consisting of

O, S and N, said groups being unsubstituted or substituted with at least one substituent selected from the group consisting of glycidyl, hydroxyl, nitro, halogen, cyano, formyl, amino, polyesters of molecular weight 500 to 100,000, polyethers of molecular weight 500 to 100,000, polyurethanes of molecular weight 500 to 100,000, and polyamides of molecular weight of 500 to 100,000;

- (c) when n is 0, m is 1, and X is —$NR_1$— ($R_1$ is hydrogen or a $C_{1-5}$ alkyl), R is a $C_{7-27}$ alkaryl or $C_{3-27}$ glycidyl group containing at least one radical selected from the group consisting of

O, S and N and having a molecular weight of 15 to 500, said groups being unsubstituted or substituted with at least one substituent selected from the group consisting of glycidyl, hydroxyl, nitro, halogen, cyano, formyl, amino, polyesters of molecular weight 500 to 100,000, polyethers of molecular weight 500 to 100,000, polyurethanes of molecular weight 500 to 100,000, and polyamides of molecular weight 500 to 100,000;

- (d) when n is 1, m is 1, and X is sulfur or —$NR_1$— ($R_1$ is hydrogen or a $C_{1-15}$ alkyl), R is a $C_{1-27}$ alkyl, $C_{3-27}$ cycloalkyl, $C_{6-27}$ aryl, $C_{7-27}$ aralkyl, $C_{7-27}$ alkaryl, $C_{3-27}$ glycidyl group, or a $C_{1-27}$ alkyl, $C_{3-27}$ cycloalkyl, $C_{6-27}$ aryl, $C_{7-27}$ aralkyl, $C_{7-27}$ alkaryl group containing at least one radical selected from the group consisting of

O, S and N and having a molecular weight of 15 to 500, said groups being unsubstituted or substituted with at least one substituent selected from the group consisting of glycidyl, hydroxyl, nitro, halogen, cyano, formyl, amino, polyesters of molecular weight 500 to 100,000, polyethers of molecular weight 500 to 100,000, polyurethanes of molecular weight 500 to 100,000, and polyamides of molecular weight of 500 to 100,000; and

- (e) when n is 0 or 1, m is an integer of 2 to 15, and X is oxygen, sulfur or —$NR_1$— ($R_1$ is hydrogen or $C_{1-5}$ alkyl), R is a residue of a $C_{1-27}$ alkyl, $C_{3-27}$ cycloalkyl, $C_{6-27}$ aryl, $C_{7-27}$ aralkyl, $C_{7-27}$ alkaryl group, or a $C_{1-27}$ alkyl, $C_{3-27}$ cycloalkyl, $C_{6-27}$ aryl, $C_{7-27}$ aralkyl, $C_{7-27}$ alkaryl, $C_{3-27}$ glycidyl group containing at least one radical selected from the group consisting of

O, S and N and having a molecular weight of 15 to 500, said groups being unsubstituted or substituted with at least one substituent selected from the groups consisting of glycidyl, hydroxyl, nitro, halogen, cyano, formyl, amino, polyesters of molecular weight 500 to 100,000, polyethers of molecular weight 500 to 100,000, polyurethanes of molecular weight 500 to 100,000, and polyamides of molecular weight of 500 to 100,000.

2. A method of producing cyclic urea derivatives as set forth in claim 1, characterized by that compounds represented by the following formula (F):

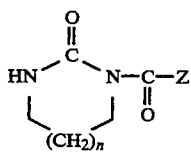
(F)

wherein Z is an alkoxylic-, aryloxylic- or aralkyloxylic group having 1 to 15 carbon atoms; n is same as in the formula (A) are reacted with compounds represented by the following formula (G):

R—(X—H)$_m$ (G)

wherein R, X and m are same as in the formula (A), to replace Z by R—X.

3. A method of producing a cyclic urea derivative represented by formula (D):

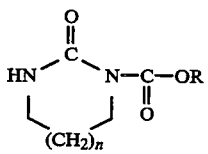
(D)

said method comprising reacting a cyclic urea represented by formula (B):

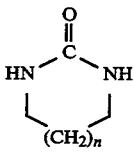
(B)

with a compound represented by formula (C):

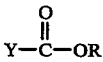
(C)

wherein in the above formulae, n is 0 or 1;
Y is halogen or OR';
R and R' are independently and alkyl, cycloalkyl, aryl, aralkyl, alkaryl or glycidyl group having 1 to 27 carbon atoms, or an alkyl, cycloalkyl, aryl, aralkyl or alkaryl group containing at least one radical selected from the group consisting of

O, S and N and having 1 to 27 carbon atoms and a molecular weight of 15 to 500, said groups being unsubstituted or substituted with at least one substituent selected from the group consisting of glycidyl, hydroxyl, nitro, halogen, cyano, formyl, amino, polyesters groups having a molecular weight 500 to 100,000, polyether groups having a molecular weight 500 to 100,000, and polyurethane groups having a molecular weight of 500 to 100,000 polyamide groups having a molecular weight of 500 to 100,000.

4. A method of producing a cyclic urea derivative represented by the formula:

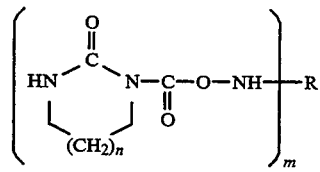

said method comprising reacting a cyclic urea represented by the formula:

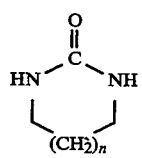

with an isocyanate compound represented by formula (E):

R—(N=C=O)$_m$ (E)

wherein in the above formulae, n is 0 or 1
m is an integer of 1 to 15; and
R is an alkyl, cycloalkyl, aryl, aralkyl, alkaryl or glycidyl group having 1 to 27 carbon atoms, or an alkyl, cycloalkyl, aryl, aralkyl or alkaryl group containing at least one radical selected from the group consisting of

O, S and N and having 1 to 27 carbon atoms and a molecular weight of 15 to 500, said groups being unsubstituted or substituted with at least one substituent selected from the group consisting of glycidyl, hydroxyl, nitro, halogen, cyano, formyl, amino, polyesters groups having a molecular weight of 500 to 100,000, polyether groups having a molecular weight of 500 to 100,000, polyurethane groups having a molecular weight of 500 to 100,000, and polyamide groups having a molecular weight of 500 to 100,000.

5. The cyclic urea derivative of claim 1, wherein m is 1.

6. The cyclic urea derivative of claim 1, wherein m is 2.

7. The cyclic urea derivative of claim 5, wherein R is said glycidyl group.

8. The cyclic urea derivative of claim 6, wherein R is said glycidyl group.

9. The cyclic urea derivative of claim 5, wherein R is 2-hydroxyethyl.

10. The cyclic urea derivative of claim 5, wherein R is benzyl.

11. The cyclic urea derivative of claim 6, wherein R is hexamethylene.

* * * * *

UNITED STATES PATENT AND TRADEMARK OFFICE
CERTIFICATE OF CORRECTION

PATENT NO. : 5,385,985
DATED : January 31, 1995
INVENTOR(S) : TSUBONIWA et al.

It is certified that error appears in the above-indentified patent and that said Letters Patent is hereby corrected as shown below:

On the cover page, item [19] error wherein "Noriyuki et al." should read --Tsuboniwa et al--;

item [75] contains typographical errors wherein "Tsuboniwa Noriyuki, Higashiosaka; Urano Satoshi, Tsuzuki; Umemoto Hirotoshi, Uji; Sakamoto Hiroyuki, Nishinomiya; Tobinaga Kenshiro, Kawanishi; Tsuchiya Yasuyuki, Hirakata, all of Japan" should read --Noriyuki Tsuboniwa, Higashiosaka; Satoshi Urano, Tsuzuki; Hirotoshi Umemoto, Uji; Hiroyuki Sakamoto, Nishinomiya; Kenshiro Tobinaga, Kawanishi; Yasuyuki Tsuchiya, Hirakata, all of Japan--.

Signed and Sealed this

Nineteenth Day of December, 1995

*Attest:*

BRUCE LEHMAN

*Attesting Officer*  *Commissioner of Patents and Trademarks*